United States Patent
Anderson

(10) Patent No.: US 9,623,234 B2
(45) Date of Patent: Apr. 18, 2017

(54) LEADLESS PACING DEVICE IMPLANTATION

(71) Applicant: Medtronic, Inc., Minneapolis, MN (US)

(72) Inventor: Kenneth M Anderson, Bloomington, MN (US)

(73) Assignee: Medtronic, Inc., Minneapolis, MN (US)

(*) Notice: Subject to any disclaimer, the term of this patent is extended or adjusted under 35 U.S.C. 154(b) by 126 days.

(21) Appl. No.: 14/538,261

(22) Filed: Nov. 11, 2014

(65) Prior Publication Data

US 2016/0129239 A1    May 12, 2016

(51) Int. Cl.
| | |
|---|---|
| *A61N 1/37* | (2006.01) |
| *A61N 1/05* | (2006.01) |
| *A61N 1/375* | (2006.01) |
| *A61M 25/09* | (2006.01) |
| *A61N 1/372* | (2006.01) |
| *A61M 25/00* | (2006.01) |
| *A61M 25/01* | (2006.01) |
| *A61N 1/368* | (2006.01) |

(52) U.S. Cl.
CPC ............ *A61N 1/056* (2013.01); *A61M 25/09* (2013.01); *A61N 1/3756* (2013.01); *A61N 1/37205* (2013.01); *A61M 25/0082* (2013.01); *A61M 25/01* (2013.01); *A61M 2025/09183* (2013.01); *A61N 1/3684* (2013.01)

(58) Field of Classification Search
CPC .................. A61N 1/059; A61B 5/6839; A61B 2018/00273
See application file for complete search history.

(56) References Cited

U.S. PATENT DOCUMENTS

| | | | |
|---|---|---|---|
| 3,486,506 A | 12/1969 | Auphan | |
| 3,659,615 A | 5/1972 | Enger | |
| 3,693,625 A | 9/1972 | Auphan | |
| 3,835,864 A | 9/1974 | Rasor et al. | |

(Continued)

FOREIGN PATENT DOCUMENTS

| | | |
|---|---|---|
| CN | 101185789 A | 5/2008 |
| CN | 101284160 A | 10/2008 |

(Continued)

OTHER PUBLICATIONS

US 8,116,861, 02/2012, Root et al. (withdrawn)

(Continued)

*Primary Examiner* — Edward Moran
*Assistant Examiner* — Natasha Patel

(57) ABSTRACT

In some examples, a system includes an implantable medical device configured for implantation in a chamber of the heart, an extension attached to the implantable medical device, the extension comprising a housing comprising at least one electrode, the housing defining a hole, and a tether comprising a first tether portion and a second tether portion and configured to be threaded through the hole. When the tether is threaded through the hole, the first tether portion and the second tether portion are on opposite sides of the hole. The tether may be used to implant the extension in a different chamber of the heart of the patient than the implantable medical device.

6 Claims, 11 Drawing Sheets

(56) References Cited

U.S. PATENT DOCUMENTS

| | | |
|---|---|---|
| 3,943,936 A | 3/1976 | Rasor et al. |
| 4,157,720 A | 6/1979 | Greatbatch |
| RE30,366 E | 8/1980 | Rasor et al. |
| 4,256,115 A | 3/1981 | Bilitch |
| 4,333,469 A | 6/1982 | Jeffcoat et al. |
| 5,170,784 A | 12/1992 | Ramon et al. |
| 5,193,539 A | 3/1993 | Schulman et al. |
| 5,193,540 A | 3/1993 | Schulman et al. |
| 5,243,977 A | 9/1993 | Trabucco et al. |
| 5,312,439 A | 5/1994 | Loeb |
| 5,324,316 A | 6/1994 | Schulman et al. |
| 5,404,877 A | 4/1995 | Nolan et al. |
| 5,405,367 A | 4/1995 | Schulman et al. |
| 5,411,535 A | 5/1995 | Fujii et al. |
| 5,441,527 A | 8/1995 | Erickson et al. |
| 5,674,259 A | 10/1997 | Gray |
| 5,792,208 A | 8/1998 | Gray |
| 5,814,089 A | 9/1998 | Stokes et al. |
| 5,843,132 A | 12/1998 | Ilvento |
| 5,895,414 A | 4/1999 | Sanchez-Zambrano |
| 5,902,331 A * | 5/1999 | Bonner ................ A61N 1/056 600/585 |
| 5,954,757 A | 9/1999 | Gray |
| 5,970,986 A | 10/1999 | Bolz et al. |
| 5,987,352 A | 11/1999 | Klein et al. |
| 6,044,300 A | 3/2000 | Gray |
| 6,051,017 A | 4/2000 | Loeb et al. |
| 6,141,588 A | 10/2000 | Cox et al. |
| 6,144,879 A | 11/2000 | Gray et al. |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,185,455 B1 | 2/2001 | Loeb et al. |
| 6,208,894 B1 | 3/2001 | Schulman et al. |
| 6,214,032 B1 | 4/2001 | Loeb et al. |
| 6,240,316 B1 | 5/2001 | Richmond et al. |
| 6,315,721 B2 | 11/2001 | Schulman et al. |
| 6,415,184 B1 | 7/2002 | Ishikawa et al. |
| 6,445,953 B1 | 9/2002 | Bulkes et al. |
| 6,592,518 B2 | 7/2003 | Denker et al. |
| 6,628,989 B1 | 9/2003 | Penner et al. |
| 6,654,638 B1 | 11/2003 | Sweeney |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,672 B2 | 5/2004 | Schulman et al. |
| 6,764,446 B2 | 7/2004 | Wolinsky et al. |
| 6,788,975 B1 | 9/2004 | Whitehurst et al. |
| 6,804,561 B2 | 10/2004 | Stover |
| 6,871,099 B1 | 3/2005 | Whitehurst et al. |
| 6,907,285 B2 | 6/2005 | Denker et al. |
| 6,917,833 B2 | 7/2005 | Denker et al. |
| 6,941,171 B2 | 9/2005 | Mann et al. |
| 6,947,782 B2 | 9/2005 | Schulman et al. |
| 7,003,350 B2 | 2/2006 | Denker et al. |
| 7,006,864 B2 | 2/2006 | Echt et al. |
| 7,024,248 B2 | 4/2006 | Penner et al. |
| 7,050,849 B2 | 5/2006 | Echt et al. |
| 7,054,692 B1 | 5/2006 | Whitehurst et al. |
| 7,082,336 B2 | 7/2006 | Ransbury et al. |
| 7,103,408 B2 | 9/2006 | Haller et al. |
| 7,114,502 B2 | 10/2006 | Schulman et al. |
| 7,120,992 B2 | 10/2006 | He et al. |
| 7,132,173 B2 | 11/2006 | Daulton |
| 7,167,751 B1 | 1/2007 | Whitehurst et al. |
| 7,177,698 B2 | 2/2007 | Klosterman et al. |
| 7,184,830 B2 | 2/2007 | Echt et al. |
| 7,198,603 B2 | 4/2007 | Penner et al. |
| 7,200,437 B1 | 4/2007 | Nabutovsky et al. |
| 7,203,548 B2 | 4/2007 | Whitehurst et al. |
| 7,214,189 B2 | 5/2007 | Zdeblick |
| 7,236,821 B2 | 6/2007 | Cates et al. |
| 7,236,829 B1 | 6/2007 | Farazi et al. |
| 7,260,436 B2 | 8/2007 | Kilgore et al. |
| 7,283,874 B2 | 10/2007 | Penner |
| 7,286,883 B2 | 10/2007 | Schulman et al. |
| 7,292,890 B2 | 11/2007 | Whitehurst et al. |
| 7,294,108 B1 | 11/2007 | Bornzin et al. |
| 7,295,879 B2 | 11/2007 | Denker et al. |
| 7,310,556 B2 | 12/2007 | Bulkes |
| 7,330,756 B2 | 2/2008 | Marnfeldt |
| 7,343,204 B2 | 3/2008 | Schulman et al. |
| 7,351,921 B1 | 4/2008 | Haller et al. |
| 7,363,082 B2 | 4/2008 | Ransbury et al. |
| 7,428,438 B2 | 9/2008 | Parramon et al. |
| 7,437,193 B2 | 10/2008 | Parramon et al. |
| 7,444,180 B2 | 10/2008 | Kuzma et al. |
| 7,450,998 B2 | 11/2008 | Zilberman et al. |
| 7,493,172 B2 | 2/2009 | Whitehurst et al. |
| 7,513,257 B2 | 4/2009 | Schulman et al. |
| 7,519,421 B2 | 4/2009 | Denker et al. |
| 7,519,424 B2 | 4/2009 | Dennis et al. |
| 7,529,589 B2 | 5/2009 | Williams et al. |
| 7,532,932 B2 | 5/2009 | Denker et al. |
| 7,532,933 B2 | 5/2009 | Hastings et al. |
| 7,535,296 B2 | 5/2009 | Bulkes et al. |
| 7,555,345 B2 | 6/2009 | Wahlstrand et al. |
| 7,558,631 B2 | 7/2009 | Cowan et al. |
| 7,565,195 B1 | 7/2009 | Kroll et al. |
| 7,587,241 B2 | 9/2009 | Parramon et al. |
| 7,606,621 B2 | 10/2009 | Brisken et al. |
| 7,610,092 B2 | 10/2009 | Cowan et al. |
| 7,616,990 B2 | 11/2009 | Chavan et al. |
| 7,616,992 B2 | 11/2009 | Dennis et al. |
| 7,617,007 B2 | 11/2009 | Williams et al. |
| 7,627,371 B2 | 12/2009 | Wang et al. |
| 7,627,376 B2 | 12/2009 | Dennis et al. |
| 7,627,383 B2 | 12/2009 | Haller et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,640,061 B2 | 12/2009 | He et al. |
| 7,647,109 B2 | 1/2010 | Hastings et al. |
| 7,650,186 B2 | 1/2010 | Hastings et al. |
| 7,706,892 B2 | 4/2010 | Colvin et al. |
| 7,713,194 B2 | 5/2010 | Zdeblick |
| 7,734,343 B2 | 6/2010 | Ransbury et al. |
| 7,747,335 B2 | 6/2010 | Williams |
| 7,751,881 B2 | 7/2010 | Cowan et al. |
| 7,766,216 B2 | 8/2010 | Daulton |
| 7,771,838 B1 | 8/2010 | He et al. |
| 7,781,683 B2 | 8/2010 | Haller et al. |
| 7,809,438 B2 | 10/2010 | Echt et al. |
| 7,822,480 B2 | 10/2010 | Park et al. |
| 7,826,903 B2 | 11/2010 | Denker et al. |
| 7,840,282 B2 | 11/2010 | Williams et al. |
| 7,848,815 B2 | 12/2010 | Brisken et al. |
| 7,848,823 B2 | 12/2010 | Drasler et al. |
| 7,860,564 B2 | 12/2010 | Root et al. |
| 7,860,570 B2 | 12/2010 | Whitehurst et al. |
| 7,890,173 B2 | 2/2011 | Brisken et al. |
| 7,894,907 B2 | 2/2011 | Cowan et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,904,167 B2 | 3/2011 | Klosterman et al. |
| 7,930,031 B2 | 4/2011 | Penner |
| 7,937,148 B2 | 5/2011 | Jacobson |
| 7,945,333 B2 | 5/2011 | Jacobson |
| 7,957,805 B2 | 6/2011 | He |
| 7,979,126 B2 | 7/2011 | Payne et al. |
| 7,991,467 B2 | 8/2011 | Markowitz et al. |
| 7,996,097 B2 | 8/2011 | DiBernardo et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,032,227 B2 | 10/2011 | Parramon et al. |
| 8,078,279 B2 | 12/2011 | Dennis et al. |
| 8,078,283 B2 | 12/2011 | Cowan et al. |
| 8,116,883 B2 | 2/2012 | Williams et al. |
| 8,126,561 B2 | 2/2012 | Chavan et al. |
| 8,127,424 B2 | 3/2012 | Haller et al. |
| 8,165,696 B2 | 4/2012 | Mcclure et al. |

(56) References Cited

U.S. PATENT DOCUMENTS

| | | |
|---|---|---|
| 8,185,212 B2 | 5/2012 | Carbunaru et al. |
| 8,204,595 B2 | 6/2012 | Pianca et al. |
| 8,224,449 B2 | 7/2012 | Carbunaru et al. |
| 8,239,045 B2 | 8/2012 | Ransbury et al. |
| 8,240,780 B1 | 8/2012 | Klimes |
| 8,295,939 B2 | 10/2012 | Jacobson |
| 8,301,242 B2 | 10/2012 | Root et al. |
| 8,301,262 B2 | 10/2012 | Mi et al. |
| 8,311,627 B2 | 11/2012 | Root et al. |
| 8,315,701 B2 | 11/2012 | Cowan et al. |
| 8,321,036 B2 | 11/2012 | Brockway et al. |
| 8,332,036 B2 | 12/2012 | Hastings et al. |
| 8,340,780 B2 | 12/2012 | Hastings et al. |
| 8,352,025 B2 | 1/2013 | Jacobson |
| 8,352,028 B2 | 1/2013 | Wenger |
| 8,359,098 B2 | 1/2013 | Lund et al. |
| 8,364,267 B2 | 1/2013 | Schleicher et al. |
| 8,364,276 B2 | 1/2013 | Willis |
| 8,364,278 B2 | 1/2013 | Pianca et al. |
| 8,364,280 B2 | 1/2013 | Marnfeldt et al. |
| 8,368,051 B2 | 2/2013 | Ting et al. |
| 8,374,696 B2 | 2/2013 | Sanchez et al. |
| 8,386,051 B2 | 2/2013 | Rys |
| 8,457,742 B2 | 6/2013 | Jacobson |
| 8,478,408 B2 | 7/2013 | Hastings et al. |
| 8,478,431 B2 | 7/2013 | Griswold et al. |
| 8,489,205 B2 | 7/2013 | Stotts et al. |
| 8,494,637 B2 | 7/2013 | Cowan et al. |
| 8,494,642 B2 | 7/2013 | Cowan et al. |
| 8,494,644 B2 | 7/2013 | Cowan et al. |
| 8,504,156 B2 | 8/2013 | Bonner et al. |
| 8,527,068 B2 | 9/2013 | Ostroff |
| 8,532,790 B2 | 9/2013 | Griswold |
| 8,541,131 B2 | 9/2013 | Lund et al. |
| 8,543,190 B2 | 9/2013 | Wasson et al. |
| 8,543,204 B2 | 9/2013 | Demmer et al. |
| 8,543,205 B2 | 9/2013 | Ostroff |
| 8,543,216 B2 | 9/2013 | Carbunaru et al. |
| 8,548,605 B2 | 10/2013 | Ollivier |
| 8,560,892 B2 | 10/2013 | Nicholes |
| 8,565,897 B2 | 10/2013 | Regnier et al. |
| 8,588,926 B2 | 11/2013 | Moore et al. |
| 8,626,294 B2 | 1/2014 | Sheldon et al. |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,922 B2 | 2/2014 | Root et al. |
| 8,660,660 B2 | 2/2014 | Dai et al. |
| 8,670,842 B1 | 3/2014 | Bornzin et al. |
| 2003/0114905 A1 | 6/2003 | Kuzma |
| 2003/0171770 A1* | 9/2003 | Kusleika .......... A61F 2/013 606/200 |
| 2004/0015204 A1 | 1/2004 | Whitehurst et al. |
| 2004/0073267 A1 | 4/2004 | Holzer |
| 2004/0093039 A1 | 5/2004 | Schumert |
| 2004/0122477 A1 | 6/2004 | Whitehurst et al. |
| 2004/0133242 A1 | 7/2004 | Chapman et al. |
| 2004/0147973 A1 | 7/2004 | Hauser |
| 2004/0162590 A1 | 8/2004 | Whitehurst et al. |
| 2004/0172089 A1 | 9/2004 | Whitehurst et al. |
| 2005/0055061 A1 | 3/2005 | Holzer |
| 2005/0070962 A1 | 3/2005 | Echt et al. |
| 2005/0256549 A1 | 11/2005 | Holzer |
| 2005/0288717 A1 | 12/2005 | Sunagawa |
| 2006/0074449 A1 | 4/2006 | Denker et al. |
| 2006/0135999 A1 | 6/2006 | Bodner et al. |
| 2006/0136005 A1 | 6/2006 | Brisken et al. |
| 2006/0173497 A1 | 8/2006 | Mech et al. |
| 2006/0241705 A1 | 10/2006 | Neumann et al. |
| 2006/0241732 A1 | 10/2006 | Denker et al. |
| 2007/0027508 A1 | 2/2007 | Cowan et al. |
| 2007/0060961 A1 | 3/2007 | Echt et al. |
| 2007/0073353 A1 | 3/2007 | Rooney et al. |
| 2007/0075905 A1 | 4/2007 | Denker et al. |
| 2007/0078490 A1 | 4/2007 | Cowan et al. |
| 2007/0088396 A1 | 4/2007 | Jacobson |
| 2007/0088397 A1 | 4/2007 | Jacobson |
| 2007/0106332 A1 | 5/2007 | Denker et al. |
| 2007/0106357 A1 | 5/2007 | Denker et al. |
| 2007/0118187 A1 | 5/2007 | Denker et al. |
| 2007/0129773 A1 | 6/2007 | Bulkes |
| 2007/0135883 A1 | 6/2007 | Drasler et al. |
| 2007/0150037 A1 | 6/2007 | Hastings et al. |
| 2007/0156204 A1 | 7/2007 | Denker et al. |
| 2007/0185538 A1 | 8/2007 | Denker et al. |
| 2007/0210862 A1 | 9/2007 | Denker et al. |
| 2007/0219590 A1 | 9/2007 | Hastings et al. |
| 2007/0276444 A1 | 11/2007 | Gelbart et al. |
| 2007/0288076 A1 | 12/2007 | Bulkes et al. |
| 2007/0288077 A1 | 12/2007 | Bulkes et al. |
| 2007/0293904 A1 | 12/2007 | Gelbart et al. |
| 2007/0293908 A1 | 12/2007 | Cowan et al. |
| 2007/0293912 A1 | 12/2007 | Cowan et al. |
| 2007/0293913 A1 | 12/2007 | Cowan et al. |
| 2008/0033497 A1 | 2/2008 | Bulkes et al. |
| 2008/0039904 A1 | 2/2008 | Bulkes et al. |
| 2008/0051854 A1 | 2/2008 | Bulkes et al. |
| 2008/0058886 A1 | 3/2008 | Williams |
| 2008/0077184 A1 | 3/2008 | Denker et al. |
| 2008/0077188 A1 | 3/2008 | Denker et al. |
| 2008/0097529 A1 | 4/2008 | Parramon et al. |
| 2008/0109054 A1 | 5/2008 | Hastings et al. |
| 2008/0119911 A1 | 5/2008 | Rosero |
| 2008/0132961 A1 | 6/2008 | Jaax et al. |
| 2008/0140154 A1 | 6/2008 | Loeb et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0319502 A1 | 12/2008 | Sunagawa et al. |
| 2009/0024180 A1 | 1/2009 | Kisker et al. |
| 2009/0048583 A1 | 2/2009 | Williams et al. |
| 2009/0082827 A1 | 3/2009 | Kveen et al. |
| 2009/0082828 A1 | 3/2009 | Ostroff |
| 2009/0171408 A1 | 7/2009 | Solem |
| 2009/0192570 A1 | 7/2009 | Jaax et al. |
| 2009/0198293 A1 | 8/2009 | Cauller et al. |
| 2009/0198295 A1 | 8/2009 | Dennis et al. |
| 2009/0198308 A1 | 8/2009 | Gross et al. |
| 2009/0326601 A1 | 12/2009 | Brisken et al. |
| 2010/0082014 A1* | 4/2010 | Jeffrey ............ A61M 25/09041 604/529 |
| 2010/0094367 A1 | 4/2010 | Sen |
| 2010/0161002 A1 | 6/2010 | Aghassian et al. |
| 2010/0179628 A1 | 7/2010 | Towe et al. |
| 2010/0249883 A1 | 9/2010 | Zdeblick |
| 2010/0249885 A1 | 9/2010 | Colvin et al. |
| 2010/0286744 A1 | 11/2010 | Echt et al. |
| 2010/0304209 A1 | 12/2010 | Lund et al. |
| 2010/0305627 A1 | 12/2010 | Anderson |
| 2010/0305628 A1 | 12/2010 | Lund et al. |
| 2010/0305629 A1 | 12/2010 | Lund et al. |
| 2010/0312320 A1 | 12/2010 | Faltys et al. |
| 2011/0054555 A1 | 3/2011 | Williams et al. |
| 2011/0060392 A1 | 3/2011 | Zdeblick et al. |
| 2011/0071585 A1 | 3/2011 | Ransbury et al. |
| 2011/0071586 A1 | 3/2011 | Jacobson |
| 2011/0077708 A1 | 3/2011 | Ostroff |
| 2011/0077721 A1 | 3/2011 | Whitehurst et al. |
| 2011/0137378 A1 | 6/2011 | Klosterman et al. |
| 2011/0160801 A1 | 6/2011 | Markowitz et al. |
| 2011/0208260 A1 | 8/2011 | Jacobson |
| 2011/0245782 A1 | 10/2011 | Berthiaume et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0313490 A1 | 12/2011 | Parramon et al. |
| 2012/0059431 A1 | 3/2012 | Williams et al. |
| 2012/0065454 A1* | 3/2012 | Kader ............ A61B 17/3468 600/8 |
| 2012/0081201 A1 | 4/2012 | Norgaard et al. |
| 2012/0095521 A1 | 4/2012 | Hintz |
| 2012/0095539 A1 | 4/2012 | Khairkhahan et al. |
| 2012/0109149 A1 | 5/2012 | Bonner et al. |
| 2012/0109236 A1 | 5/2012 | Jacobson et al. |

(56) References Cited

U.S. PATENT DOCUMENTS

| | | |
|---|---|---|
| 2012/0116489 A1 | 5/2012 | Khairkhahan et al. |
| 2012/0143271 A1 | 6/2012 | Root et al. |
| 2012/0158090 A1 | 6/2012 | Chavan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1* | 7/2012 | Grubac ............... A61N 1/3756 606/129 |
| 2012/0179219 A1 | 7/2012 | Kisker et al. |
| 2012/0197352 A1 | 8/2012 | Carbunaru et al. |
| 2012/0197373 A1 | 8/2012 | Khairkhahan et al. |
| 2012/0232371 A1 | 9/2012 | Mech et al. |
| 2012/0290021 A1 | 11/2012 | Saurkar et al. |
| 2012/0290025 A1 | 11/2012 | Keimel |
| 2012/0316622 A1 | 12/2012 | Whitehurst et al. |
| 2012/0323099 A1 | 12/2012 | Mothilal et al. |
| 2012/0323219 A1* | 12/2012 | Huntoon ............ A61B 17/7061 604/506 |
| 2013/0023975 A1 | 1/2013 | Locsin |
| 2013/0030483 A1 | 1/2013 | Demmer et al. |
| 2013/0035748 A1 | 2/2013 | Bonner et al. |
| 2013/0066169 A1 | 3/2013 | Rys et al. |
| 2013/0073004 A1 | 3/2013 | Root et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103109 A1 | 4/2013 | Jacobson |
| 2013/0110127 A1 | 5/2013 | Bornzin et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0123872 A1 | 5/2013 | Bornzin et al. |
| 2013/0123875 A1 | 5/2013 | Varady et al. |
| 2013/0131159 A1 | 5/2013 | Ko et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0184790 A1 | 7/2013 | Schleicher et al. |
| 2013/0226259 A1 | 8/2013 | Penner et al. |
| 2013/0231710 A1 | 9/2013 | Jacobson |
| 2013/0234692 A1 | 9/2013 | Liang et al. |
| 2013/0235663 A1 | 9/2013 | Walsh et al. |
| 2013/0235672 A1 | 9/2013 | Walsh et al. |
| 2013/0238044 A1 | 9/2013 | Penner |
| 2013/0238056 A1 | 9/2013 | Poore et al. |
| 2013/0238072 A1 | 9/2013 | Deterre et al. |
| 2013/0238073 A1 | 9/2013 | Makdissi et al. |
| 2013/0238840 A1 | 9/2013 | Walsh et al. |
| 2013/0253309 A1 | 9/2013 | Allan et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0302665 A1 | 11/2013 | Zhao et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012342 A1 | 1/2014 | Penner et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0026016 A1 | 1/2014 | Nicholes |
| 2014/0031836 A1 | 1/2014 | Ollivier |
| 2014/0031837 A1 | 1/2014 | Perryman et al. |
| 2014/0039570 A1 | 2/2014 | Carroll et al. |
| 2014/0039578 A1 | 2/2014 | Whitehurst et al. |
| 2014/0039588 A1 | 2/2014 | Ok et al. |
| 2014/0039591 A1 | 2/2014 | Drasler et al. |
| 2014/0046395 A1 | 2/2014 | Regnier et al. |
| 2014/0058240 A1 | 2/2014 | Mothilal et al. |
| 2014/0072872 A1 | 3/2014 | Hodgkinson et al. |
| 2014/0100627 A1 | 4/2014 | Min |
| 2014/0107723 A1 | 4/2014 | Hou et al. |
| 2014/0172034 A1 | 6/2014 | Bornzin et al. |

FOREIGN PATENT DOCUMENTS

| | | |
|---|---|---|
| EP | 1541191 A1 | 6/2005 |
| TW | 1251986 B | 3/2006 |
| TW | 1252007 B | 3/2006 |
| WO | 2006099425 A1 | 9/2006 |
| WO | 2009006531 A1 | 1/2009 |
| WO | 2009052480 A2 | 4/2009 |
| WO | 2012150000 A2 | 11/2012 |
| WO | 2012154599 A2 | 11/2012 |
| WO | 2013080038 A2 | 6/2013 |
| WO | 2014046662 A1 | 3/2014 |

OTHER PUBLICATIONS (PCT/US2015/058753) PCT Notification of Transmittal of the International Search Report and the Written Opinion of the International Searching Authority, mailed Jan. 29, 2016, 12 pages.

* cited by examiner

LEADLESS PACING DEVICE IMPLANTATION

TECHNICAL FIELD

The disclosure relates to cardiac pacing, and more particularly, to cardiac pacing using a pacing device implanted within the heart.

BACKGROUND

An implantable pacemaker may deliver pacing pulses to a patient's heart and monitor conditions of the patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at a target site. The pulse generator may provide electrical stimulation to the target site and/or monitor cardiac electrical activity at the target site via the electrodes.

A leadless pacing device has also been proposed for sensing electrical activity and/or delivering therapeutic electrical signals to the heart. The leadless pacing device may include one or more electrodes on its outer housing to deliver therapeutic electrical signals and/or sense intrinsic depolarizations of the heart. The leadless pacing device may be positioned within or outside of the heart and, in some examples, may be anchored to a wall of the heart via a fixation mechanism.

SUMMARY

The disclosure describes devices, systems, and methods for implanting a cardiac pacing system that includes an implantable medical device (hereinafter, "IMD") configured for implantation within a chamber of a heart of a patient, and an extension extending from a housing of the IMD, which is also configured to be implanted within the heart. The extension includes one or more electrodes with which the IMD may sense electrical cardiac activity and/or provide electrical stimulation. The extension is electrically coupled to a sensing module and/or a stimulation module of the IMD. In some examples, the IMD is configured to be implanted in a first chamber of a heart of a patient (e.g., the right ventricle), and a portion of the extension may be configured to position at least one electrode within or proximate to another chamber of the heart (e.g., the left ventricle), thereby allowing the IMD to deliver biventricular pacing in a patient or to sense electrical activity in at least two chambers of the heart.

In some example, the extension includes a housing that includes one or more electrodes configured to be positioned at a target site within the heart that is within or proximate to a chamber of the heart other than the one in which the IMD is implanted. The housing may define an opening, through which a tether may be threaded. The tether, in conjunction with a guidewire and a pusher, may be used to guide the housing to the target site. In some examples, a proximal end (or a proximal portion) of the guidewire is mechanically connected to a distal end of the tether, such that as the tether is pulled through the hole defined by the housing in a proximal direction, the guidewire is threaded through the hole. In this way, the housing may be threaded through the guidewire and may be guided to the target site via the guidewire.

In some examples, the tether may also be threaded through an eyelet or other opening defined by a pusher. As the tether is pulled through the hole defined by the housing in a proximal direction and the guidewire is threaded through the hole, the guidewire is also threaded through the eyelet defined by the pusher. The pusher is configured to engage with a proximal side of the housing to apply a force to push the housing in a distal direction, towards the target site.

In one example, the disclosure is directed to a system comprising an implantable medical device configured to be implanted in a chamber of a heart of a patient; an extension attached to the implantable medical device, the extension comprising a housing comprising at least one electrode, the housing defining a hole; and a tether comprising a first tether portion and a second tether portion and configured to be threaded through the hole, wherein when the tether is threaded through the hole, the first tether portion and the second tether portion are on opposite sides of the hole.

In another example, the disclosure is directed to a method comprising introducing an implantable medical device to a first chamber of a heart of a patient via a femoral vein, wherein the implantable medical device is attached to an extension comprising a housing including at least one electrode, the housing defining a hole, and wherein a tether is threaded through the hole, the tether including a first tether portion and a second tether portion on an opposite side of the hole from the first tether portion; directing a guidewire to a target vein, the guidewire comprising a first guidewire portion and a second guidewire portion, the second guidewire portion comprising a thread attached to the second tether portion; introducing a pusher up the second tether portion to a position proximate to the housing; removing the tether from the patient by at least pulling the second tether portion to replace the tether with the guidewire; pushing the housing along the guidewire using the pusher.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
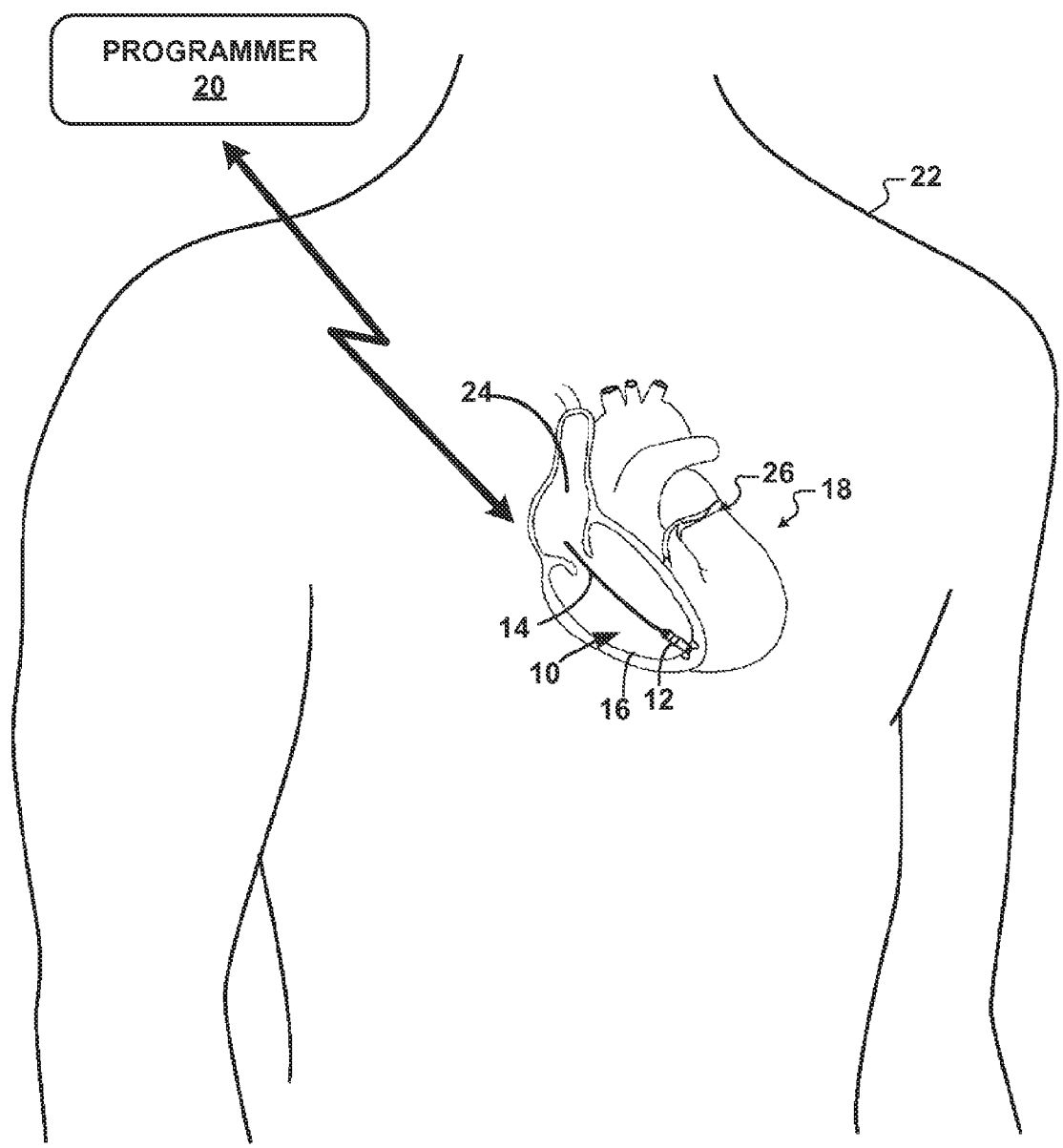
FIG. 1 is a conceptual diagram illustrating an example cardiac pacing system that comprises an implantable medical device (IMD) and an extension.

This disclosure is directed to a system and method for implanting a cardiac pacing system capable of providing biventricular pacing to a patient. The system comprises an IMD which is configured to be implanted in a chamber of the heart, and an extension or lead including one or more electrodes, also configured for placement within the heart, e.g., in a different chamber than the IMD. In some examples, the system and method are configured to modify a leadless pacing device (LPD) in a manner so that it may provide biventricular pacing.

For example, an extension that includes one or more electrodes may be mechanically connected to a housing of the LPD such that it extends from the housing, and the one or more electrodes may be electrically connected to a sensing module of the LPD, a stimulation module of the LPD, or both the sensing and stimulation modules. In some examples, the extension includes two electrodes, although any suitable number of electrodes may be used in other examples. For example, a proximate electrode (closer to the LPD) may be positioned approximately 3-10 centimeters (cm) from the distal end of the LPD and a distal electrode may be positioned approximately 20-25 cm from the distal end of the LPD. The electrodes of the extension may be used for sensing electrical cardiac signals, delivering electrical stimulation, or both. In some examples, the LPD may be programmed to sense atrial signals via the proximate electrode and to provide pacing stimulation pulses via the distal electrode.

In some examples, at least one electrode (e.g., the distal electrode) of the extension may be positioned on a housing that is attached to the extension. In some examples the IMD is implanted in the right ventricle. One or more electrodes on the IMD may provide electrical stimulation to the right ventricle, as well as sense electrical signals from the ventricle. In addition, in some examples in which the IMD is implanted in the right ventricle, the distal electrode of the extension may be implanted in a contrary vein via the coronary sinus. In some examples, the coronary sinus is accessed from the inferior vena cava.

The housing of the extension may include one or more features that aid the implantation of the housing in a chamber of a heart of the patient, e.g., aid in the control of the housing position relative to the chamber. For example, the housing may define a hole that includes a central axis that is parallel to the longitudinal axis of the extension. A tether may be installed through the hole. The tether may be position such that a first portion of the tether is one side of the housing and a second portion of the tether is on the other side of the housing.

The tether may help control the position of the housing, and, therefore, aid in proper positioning of the extension relative to a target stimulation site (e.g., a left ventricle). For example, a clinician implanting the system in a patient may pull on the tether to help move the housing of the extension in a first direction, e.g., towards the clinician, and may also use a pusher to move the housing in a second direction opposite the first direction. In some examples, the pusher may include an eyelet or another feature at a distal end that is configured to engage with the housing to apply a force against the housing to move the housing in the second direction.

In some examples, a guidewire may further aid in the implantation of the distal electrode of the extension in a patient. In some examples, a guidewire including a first guidewire portion, e.g., which may be defined by a standard guidewire, and a second guidewire portion. The second guidewire portion may be or may comprise, for example, a suture thread or another material that is more flexible than the first guidewire portion. A proximal end of the second guidewire portion may be attached to a proximal end of the first tether portion.

In examples in which the second guidewire portion comprises a suture thread, a stiffening tube may be used to stiffen the second guidewire portion while the guidewire is being placed. The stiffening tube can be, for example, formed from a biocompatible plastic or another material that is more stiff than the second guidewire portion. A clinician may be guide the guidewire to the target chamber of the heart of the patient using a catheter that defines a pathway for the guidewire, and, after the distal end of the first guidewire portion is placed at the desired location within the patient, the stiffening tube may be removed from the patient along with the catheter.

A clinician may introduce a pusher into the patient, e.g., by threading a distal end of the pusher on the second tether portion and then pushing the pusher along the second tether portion to a position proximate the housing of the extension. The pusher is relatively stiff and is configured to apply a force against the housing of the extension to help change the position of the housing within the patient. In some examples, the pusher may be made of wire and may include an eyelet at the end, the eyelet being configured to receive the tether and the guidewire. In some examples, the eyelet may be closed, such that only the end of the tether may be threaded through the eyelet. This may be referred to as a threading in a longitudinal direction. In other examples, the eyelet may be open, such that the tether may be threaded through the eyelet in either the longitudinal direction or a lateral direction, in which a section of the tether between the proximal and distal ends may be introduced into the eyelet through the opening.

The pusher may be used to push the electrode through an introducer to the target position within a heart of the patient, e.g., into the right atrium or another chamber. At the proximal end of the introducer, the proximal end of the thread may be attached to the first tether portion. A clinician may pull on the second tether portion, e.g., in a direction towards the clinician to remove the tether from the hole. Because the second guidewire portion is mechanically connected to the first tether portion, once the tether has been removed, the guidewire replaces the tether within the hole in the housing. The clinician may then use pusher to push the housing along the guidewire to the target location within the patient.

For fine adjustments to the electrode location once the housing approaches the end of the guidewire, the clinician may push on the pusher to move the electrode distally (in a direction away from the clinician) or pull on both the guidewire and the pusher to move the electrode in the proximal direction (in a direction towards the clinician).

A cardiac pacing system consistent with the present disclosure may be contained with the patient's heart once implanted. By locating the IMD and the extension in the heart, the risk of lead fracture along the path from the IMD implant location to the heart is eliminated.

FIG. 1 is a conceptual diagram illustrating an example cardiac pacing system 10 that comprises an implantable medical device (IMD) 12 and an extension 14 implanted in patient 22. In some examples, IMD 12 is a leadless pacing device because IMD 12 is not connected to any leads that extend outside of heart 18. Extension 14 is configured to position a first electrode (not shown) proximate to or within a chamber of heart 18 other than the one in which IMD 12 implanted. In the example shown in FIG. 1, IMD 12 is implanted in right ventricle 16 of heart 18 of patient 22. More particularly, IMD 12 is fixed or attached to the inner wall of the right ventricle 16 proximate to the apex of the right ventricle in the example of FIG. 1. In other examples, IMD 12 may be fixed to the inner wall of right ventricle 16 at another location, e.g., on the intraventricular septum or free-wall of the right ventricle, or may be fixed to the outside of heart 18, i.e., epicardially, proximate to right ventricle 16. In other examples, IMD may be fixed within, on, or near the left-ventricle of heart 18.

In the example shown in FIG. 1, extension 14 is configured to extend away from IMD 12 and into coronary sinus 26 when IMD 12 is implanted in an apex of right ventricle 16. In some examples, extension 14 may have a length that permits extension 14 to reach a target vein within the coronary sinus 26 in order for at least one electrode of extension 14 to provide electrical stimulation to the left ventricle of heart 18. For example, extension 14 may have a length of approximately 25 centimeters (cm) (as measured from the proximal end connected to IMD to a distal most electrode of extension 14). In some examples, extension 14 may have a relatively small cross-sectional dimension (where the cross-section is taken in a direction perpendicular to a longitudinal axis of extension 14) and flexible enough to permit the tricuspid valve to sufficiently close around extension 14 to prevent backflow into right atrium 24 from right ventricle 16. For example, extension 14 may be about 4 French (i.e., about 1.33 millimeters (mm)) in diameter. In some examples, extension 14 may include a first portion approximately 4 French in diameter and a second, more distal, portion about 2 French (i.e., about 0.66 mm) in diameter.

In the example shown in FIG. 1, IMD 12 is configured to electrical activity of right atrium 24, right ventricle 16 and/or the left ventricle (via an electrode in the coronary sinus). IMD 12 may also be configured to generate and delivering pacing stimulation to both the right and left ventricles. In some examples, the most distal electrode (not shown) of extension 14 is affixed to heart 18 via coronary sinus 26 while a second electrode of extension 14 is not affixed to cardiac tissue. Extension 14 is configured to continue to extend away from IMD 12 towards right atrium 24, even in the presence of blood flow from right atrium 24 to right ventricle 16.

Also shown in FIG. 1 is medical device programmer 20, which is configured to program IMD 12 and retrieve data from IMD 12. Programmer 20 may be a handheld computing device, desktop computing device, a networked computing device, etc. Programmer 20 may include a computer-readable storage medium having instructions that cause a processor of programmer 20 to provide the functions attributed to programmer 20 in the present disclosure. IMD 12 may wirelessly communicate with programmer 20. For example, IMD 12 may transfer data to programmer 20 and may receive data from programmer 20. Programmer 20 may also wirelessly program and/or wirelessly charge IMD 12.

Data retrieved from IMD 12 using programmer 20 may include cardiac EGMs stored by IMD 12 that indicate electrical activity of heart 18 and marker channel data that indicates the occurrence and timing of sensing, diagnosis, and therapy events associated with IMD 12. Data transferred to IMD 12 using programmer 20 may include, for example, operational programs for IMD 12 that causes IMD 12 to operate as described herein.

Pacing system 10 may be implanted in right ventricle 16 or another chamber of heart 18, using any suitable technique. In some cases, pacing system 10 may be implanted according to the method discussed below with respect to FIGS. 4A-4F and 5. As described in further detail below, in some examples, extension 14 includes a feature configured to facilitate control of the extension during implantation of the extension in the heart. For example, extension 14 may include a housing that defines a hole or extension 14 may otherwise define an opening through which a tether may be thread. For example, extension 14 may include an eyelet proximate a distal most electrode of extension 14. A tether may be fed through the hole or eyelet during implantation of IMD 12 and extension 14 in heart 18. The tether may provide a physical connection to extension 14 that may be used to control the positioning of a distal portion of extension 14. For example, the tether may be used to position a pusher and a guidewire proximate the distal portion of the guidewire; the pusher and guidewire may then be used to control the position of the distal most portion of extension 14 relative to heart 18. After implantation, the guidewire, the tether and the pusher are removed from patient 22.

Figure 2:
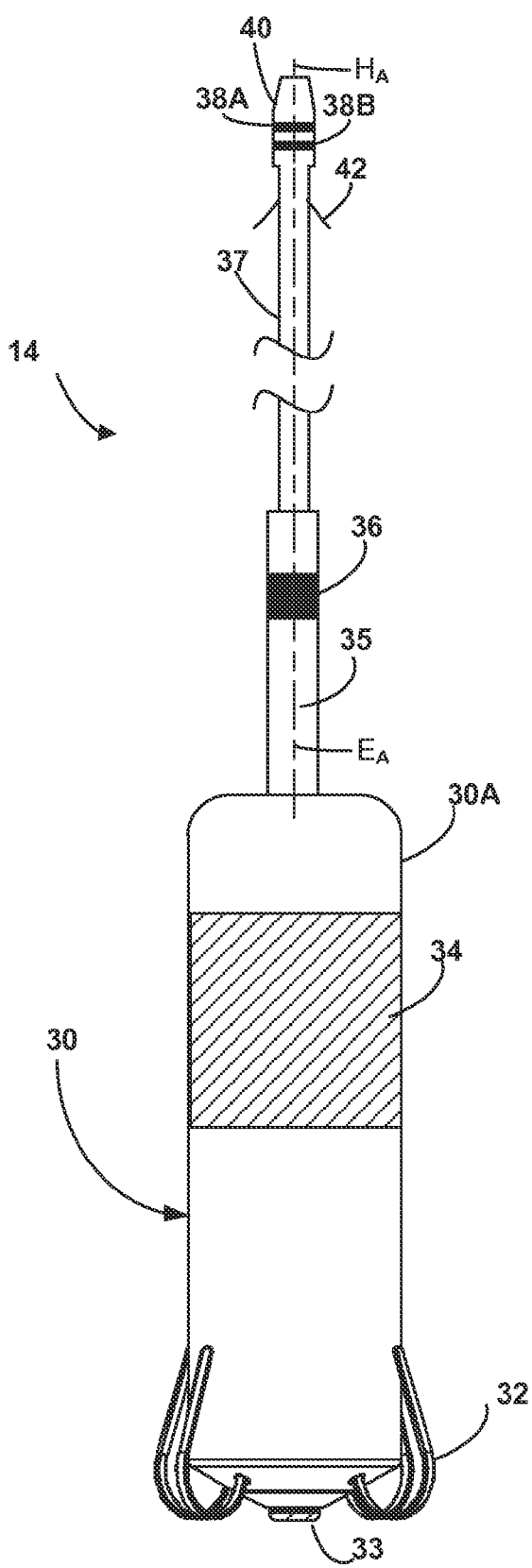
FIG. 2 is a conceptual illustration of another example cardiac pacing system that includes an IMD and an extension.

FIG. 2 is a conceptual illustration of an example pacing system 10 that includes IMD 12 and extension 14. IMD 12 is configured to be implanted within a chamber of a heart of a patient, e.g., to monitor electrical activity of the heart and/or provide electrical therapy to the heart. In the example shown in FIG. 2, IMD 12 includes outer housing 30, a plurality of fixation tines 32 and electrodes 33 and 34. Extension 14 includes electrodes 36 and 38A, 38B, housing 40 and fixation elements 42.

Outer housing 30 has a size and form factor that allows IMD 12 to be entirely implanted within a chamber of a heart of a patient. In some examples, outer housing 16 may have a cylindrical (e.g., pill-shaped) form factor. IMD 12 may include a fixation mechanism configured to fix IMD 12 to cardiac tissue. For example, in the example shown in FIG. 2, IMD 12 includes fixation tines 32 extending from housing 30 and configured to engage with cardiac tissue to substantially fix a position of housing 30 within the chamber of the heart 18. Fixation tines 32 are configured to anchor housing 30 to the cardiac tissue such that IMD 12 moves along with the cardiac tissue during cardiac contractions. Fixation tines 32 may be fabricated from any suitable material, such as a shape memory material (e.g., Nitinol). Although IMD 12 includes a plurality of fixation tines 32 that are configured to anchor IMD 12 to cardiac tissue in a chamber of a heart, in other examples, IMD 12 may be fixed to cardiac tissue using other types of fixation mechanisms, such as, but not limited to, barbs, coils, and the like.

Housing 30 houses electronic components of IMD 12, e.g., a sensing module for sensing cardiac electrical activity via one ore more combinations of electrodes 33, 34, 36 38A, and 38B and an electrical stimulation module for delivering electrical stimulation therapy via one or more combinations of electrodes 33, 34, 36, 38A, and 38B. Electronic components may include any discrete and/or integrated electronic circuit components that implement analog and/or digital circuits capable of producing the functions attributed to IMD 12 described herein. In some examples, housing 30 may also house components for sensing other physiological parameters, such as acceleration, pressure, sound, and/or impedance. Although shown with both electrodes 33 and 34, in some examples, housing 30 may only include one or the other of electrodes 33 and 34.

Additionally, housing 30 may also house a memory that includes instructions that, when executed by one or more processors housed within housing 30, cause IMD 12 to perform various functions attributed to IMD 12 herein. In some examples, housing 30 may house a communication module that enables IMD 12 to communicate with other electronic devices, such as a medical device programmer. In some examples, housing 30 may house an antenna for wireless communication. Housing 30 may also house a power source, such as a battery. Housing 30 can be hermetically or near-hermetically sealed in order to help prevent fluid ingress into housing 30.

IMD 12 is configured to sense electrical activity of the heart and deliver electrical stimulation to the heart via one or more combinations of electrodes 33, 34, 36, 38A, and 38B. In some examples, sensing of electrical activity occurs via a first combination of electrodes and delivery of electrical stimulation occurs via a second, different, combination of electrodes. IMD 12 comprises electrodes 33 and 34 and extension 14 comprises electrodes 36, 38A, and 38B. Although shown with three electrodes 36, 38A, and 38B in FIG. 2, in some examples, extension 14 may only include distal electrode 38A, or may include only electrodes 38A, 38B on housing 40.

Electrodes 33 and 34 may be mechanically connected to housing 30. As another example, electrodes 33 and 34 may be defined by an outer portion of housing 30 that is electrically conductive. For example, electrode 34 may be defined by conductive portion 30A of housing 30. Conductive portion 30A may, in some examples, define at least part of a power source case that houses a power source (e.g., a battery) of IMD 12. The power source case may house a power source (e.g., a battery) of IMD 12. Electrodes 33 and 34 are electrically isolated from each other. Electrode 33 may be referred to as a tip electrode, and fixation tines 32 may be configured to anchor IMD 12 to cardiac tissue such that electrode 33 maintains contact with the cardiac tissue. In some examples, a portion of housing 30 may be covered by, or formed from, an insulative material to isolate electrodes 33 and 34 from each other and/or to provide a desired size and shape for one or both of electrodes 33 and 34.

Extension 14 is configured to position electrodes 36, 38A, 38B, or just electrodes 38A, 38B within a chamber other than the one in which IMD 12 is implanted. In this way, extension 14 may extend the sensing and pacing capabilities of system 10. In the example shown in FIG. 1, electrode 36 is electrically connected to at least some electronics of IMD 12 (e.g., a sensing module and a stimulation module) via an electrical conductor of extension 14 and an electrically conductive portion 30A of housing 30 of IMD 12, the electrically conductive portion 30A being electrically isolated from electrode 33, but electrically connected to electrode 34. As a result, electrodes 34, electrode 36 may have the same polarity and are electrically common. Conductive portion 30A of housing 16 may be electrically connected to at least some electronics of LPD 12 (e.g., a sensing module, an electrical stimulation module, or both), such that conductive portion 30A defines part of an electrically conductive pathway from electrode 36 to the electronics.

Electrodes 38A, 38B are also electrically connected to at least some electronics of IMD 12 (e.g., a sensing module and a stimulation module) via one or more electrical conductors of extension 14. In some examples, electrodes 38A, 38B are electrically connected to at least some electronics of IMD 12 via different electrodes. In addition, in some examples, one or both of electrodes 38A, 38B may be electrically common with electrode 34 and/or electrode 36.

Extension 14 includes a first extension portion 35 and a second extension portion 37. In the example shown in FIG. 2, electrode 36 is carried by a first extension portion 35 of extension 14, and is located at a distal portion of first extension portion 35, the distal being further from IMD 12 than a proximal portion. In some examples, first extension portion 35 may be a self-supporting body and is between approximately 5 cm and 12 cm in length. In other examples, however, electrode 36 may have another position relative to first extension portion 35, such mid-way between housing 30 and the distal end of first extension portion 35, or otherwise away from the distal end of first extension portion 35. In some examples, a center of electrode 36 may be between approximately 3 cm and 10 cm from the distal end of IMD 12 (i.e., the end closest to extension 14). In some examples, a center of electrode 36 may be approximately 10 cm from the distal end of IMD 12.

In some examples, IMD 12 senses electrical activity of right atrium 24 of heart 18 of patient 22 via electrode 36; extension 14 may be configured such that when IMD 12 is implanted in right ventricle 16, electrode 36 is located within right atrium 24. Electrode 36 may have any suitable configuration. For example, electrode 36 may have a ring-shaped configuration, or a partial-ring configuration. Electrode 36 may be formed from any suitable material, such as a titanium nitride coated metal.

Second extension portion 37 is distal to first extension portion 35, such that first extension portion 35 is positioned between IMD 12 and second extension portion 37. In some examples, second portion 37 has a cross-sectional dimension (e.g., a diameter) approximately equal to the diameter of first portion 35. For example, the diameter of second extension portion 37 may be approximately 4 French. In other examples, second extension portion 37 has a cross-sectional dimension smaller then the cross-sectional dimension of first extension portion 35. For example, the diameter of second extension portion 37 may be approximately 2 French.

In some examples, first and second extension portions 35, 37 are configured such that when IMD 12 is implanted in right ventricle 16, electrodes 38A, 38B and housing 40 of extension 14 are implanted in a left ventricle of heart 18. For example, the length of second extension portion 37 may be approximately 15 cm to 20 cm, and extension 14 may have a total length of approximately 20 cm to 25 cm.

Electrodes 38A, 38B are located at the distal end of second extension portion 37 on a housing 40. Housing 40 may include a hole or eyelet that includes a central axis $H_A$ that is parallel to a longitudinal axis $E_A$ of extension 14. The hole or eyelet may be configured to receive tether and/or a guidewire. Electrodes 38A, 38B may have any suitable configuration. For example, electrodes 38A, 38B may each be a ring-shaped configuration, or a partial-ring configuration. Electrodes 38A, 38B may be formed from any suitable material, such as a titanium nitride coated metal. Although housing 40 including two electrodes 38A, 38B are shown in FIG. 2, in other examples of system 10, housing 40 may include any suitable number of electrodes, such as one or more than two electrodes.

Second portion 37 of extension 14 may also include one or more fixation elements 42 configured to engage with tissue to substantially fix a position of electrodes 38A, 38B relative to heart 18 of patient 22. Fixation elements 42 may be any suitable type of fixation element, such as tines, double-bended elements, s-curve element, barbs, coils, or the like.

The relative spacing between electrodes 36, 38A, 38B may vary based on the type of stimulation and/or sensing system 10 is configured to provide. In some examples, electrode 36 is spaced from electrodes 38A, 38B along extension 14 such that when implanted system 10 is implanted in heart 22, electrode 36 is located within the right atrium, and electrodes 38A, 38B are located within the coronary sinus proximate to the left ventricle. In this example, system 10 may be used to sense electrical activity in both right ventricle 16 and the left ventricle, as well as deliver electrical stimulation to both right ventricle 16 and left ventricle, e.g., to provide biventricular pacing therapy.

Figure 3:
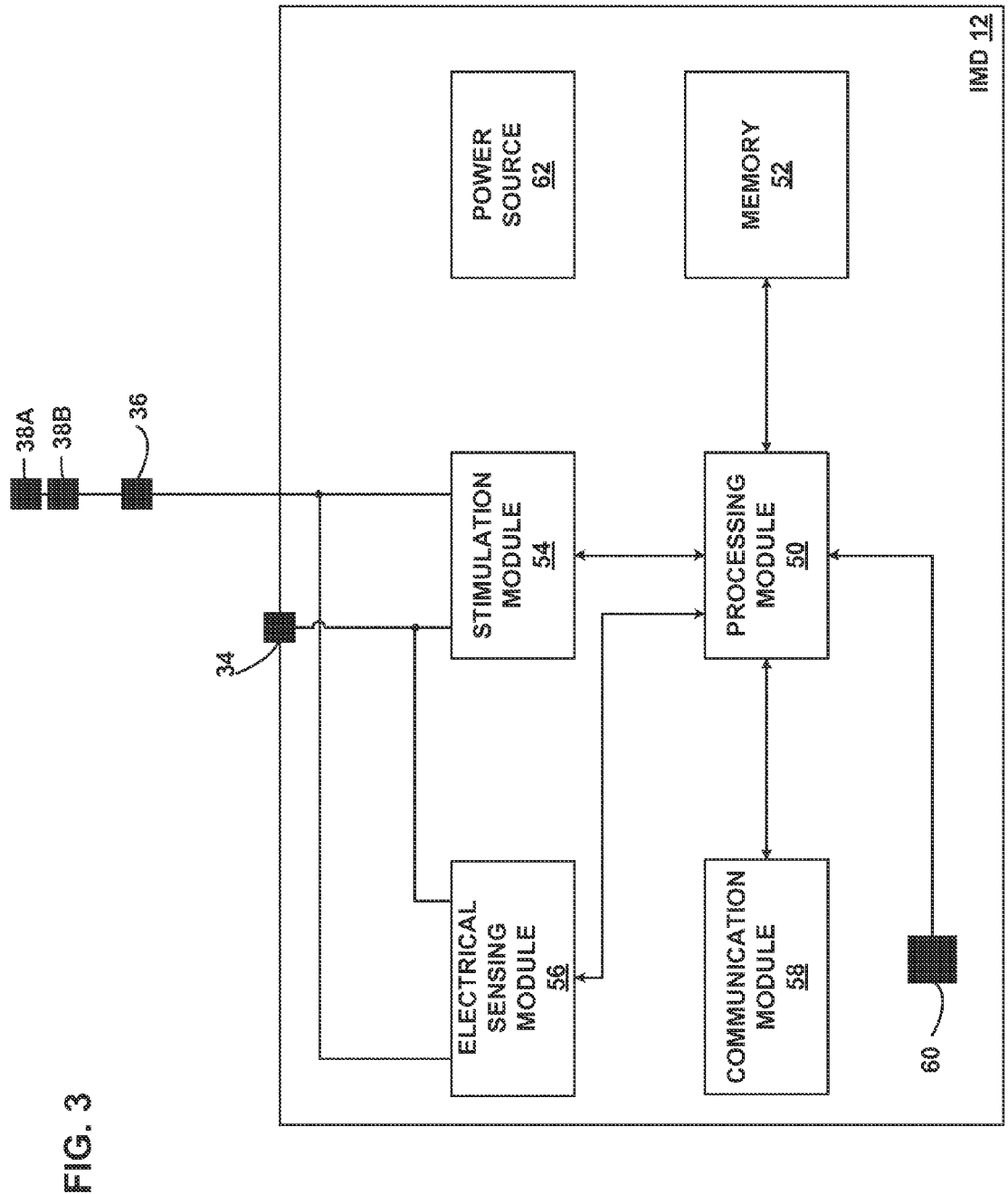
FIG. 3 is a functional block diagram of an example IMD.

FIG. 3 is a functional block diagram of an example IMD 12. IMD 12 includes a processing module 50, memory 52, stimulation module 54, electrical sensing module 56, communication module 58, sensor 60, and power source 62. Power source 62 may include a battery, e.g., a rechargeable or non-rechargeable battery.

Modules included in IMD 12 represent functionality that may be included in IMD 12 of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, and the like. The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 50 may include any one or more of a microprocessor, a controller, a digital signal processor (DSP), an application specific integrated circuit (ASIC), a field-programmable gate array (FPGA), or equivalent discrete or integrated logic circuitry. In some examples, processor 50 may include multiple components, such as any combination of one or more microprocessors, one or more controllers, one or more DSPs, one or more ASICs, or one or more FPGAs, as well as other discrete or integrated logic circuitry.

Processing module 50 may communicate with memory 52. Memory 52 may include computer-readable instructions that, when executed by processing module 50, cause processing module 50 to perform the various functions attributed to processing module 50 herein. Memory 52 may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory 52 may include instructions that, when executed by one or more processors, cause the modules to perform various functions attributed to the modules herein. For example, memory 52 may include pacing instructions and values. The pacing instructions and values may be updated by programmer 20 (FIG. 1).

Stimulation module 54 and electrical sensing module 56 are electrically coupled to electrodes 33, 34, 36, 38A, 38B. Processing module 50 is configured to control stimulation module 54 to generate and deliver electrical stimulation to heart 18 (e.g., right ventricle 16 and the left ventricle via coronary sinus 26 in the example shown in FIG. 1) via a selected subset of electrodes 33, 34, 36, 38A, 38B. For example, stimulation module 54 may deliver pacing electrical stimulation to right ventricle 16 via electrodes 33 and 34, which are configured to be implanted within right ventricle 16. As another example, stimulation module 54 may deliver pacing electrical stimulation to the left ventricle via electrodes 38A, 38B, which are configured to be implanted within the left ventricle. Electrical stimulation may include, for example, pacing pulses, or any other suitable electrical stimulation. Processing module 50 may control stimulation module 54 to deliver electrical stimulation therapy via a selected subset of electrodes 33, 34, 36, 38A, 38B according to one or more therapy programs including pacing instructions that define a ventricular pacing rate, which may be stored in memory 52.

In addition, processing module 50 is configured to control electrical sensing module 56 monitor signals from any suitable subset of electrodes 33, 34, 36, 38A, 38B in order to monitor electrical activity of heart 18. For example, electrical sensing module 56 may sense electrical activity within right ventricle 16 via electrodes 33, 34, may sense electrical activity within right atrium 24 via electrodes 33, 36, may sense electrical activity within the right ventricle via electrodes 38A, 38B, or any combination of the aforementioned sensing may be performed by sensing module 56.

Electrical sensing module 56 may include circuits that acquire electrical signals. Electrical sensing module 56 may acquire electrical signals form a subset of electrodes 33, 34, 36 and 38A, 38B. Electrical signals acquired by electrical sensing module 56 may include intrinsic cardiac electrical activity, such as intrinsic atrial depolarization and/or intrinsic ventricular depolarization. Electrical sensing module 56 may filter, amplify, and digitize the acquired electrical signals to generate raw digital data. Processing module 50 may receive the digitized data generated by electrical sensing module 56. In some examples, processing module 50 may perform various digital signal processing operations on the raw data, such as digital filtering.

Processing module 50 may sense cardiac events based on the data received from electrical sensing module 56. For example, processing module 50 may sense atrial electrical activity based on the data received from electrical sensing module 56. For example, in examples in which IMD 12 and extension 14 are implanted in right ventricle 16, processing module 50 may detect P-waves indicative of atrial activation events based on the data received from electrical sensing module 56 via electrodes 33, 36. In some examples, processing module 50 may also sense ventricular electrical activity based on the data received from electrical sensing module 56. For example, processing module 50 may detect R-waves indicative of right ventricular activation events based on the data received from electrical sensing module 56 via electrodes 33, 34. In examples in which processor 50 uses multiple electrodes for both R-wave and P-wave sensing, processor 50 may detect the R-waves and P-waves from the same sensed signal. The sensing vector can be between electrodes 33 and 36, for example. As another example, processing module 50 may detect a signal characteristic indicative of left ventricular activation events based on the data received from electrical sensing module 56 via electrodes 38A, 38B, or via electrodes 36, 38A, or via electrodes 36, 38B.

In some examples, in addition to electrical sensing module 56, IMD 12 includes sensor 60, which may comprise at least one of a variety of different sensors. For example, sensor 60 may comprise at least one of a pressure sensor and an accelerometer. Sensor 60 may generate signals that indicate at least one of parameter of patient 22, such as, but not limited to, at least one of: an activity level of patient 22, a hemodynamic pressure, and heart sounds.

Communication module 58 may include any suitable hardware (e.g., an antenna), firmware, software, or any combination thereof for communicating with another device, such as programmer 20 (FIG. 1) or a patient monitor. Under the control of processing module 50, communication module 58 may receive downlink telemetry from and send uplink telemetry to other devices, such as programmer 2 or a patient monitor, with the aid of an antenna included in communication module 58.

Figure 4A:
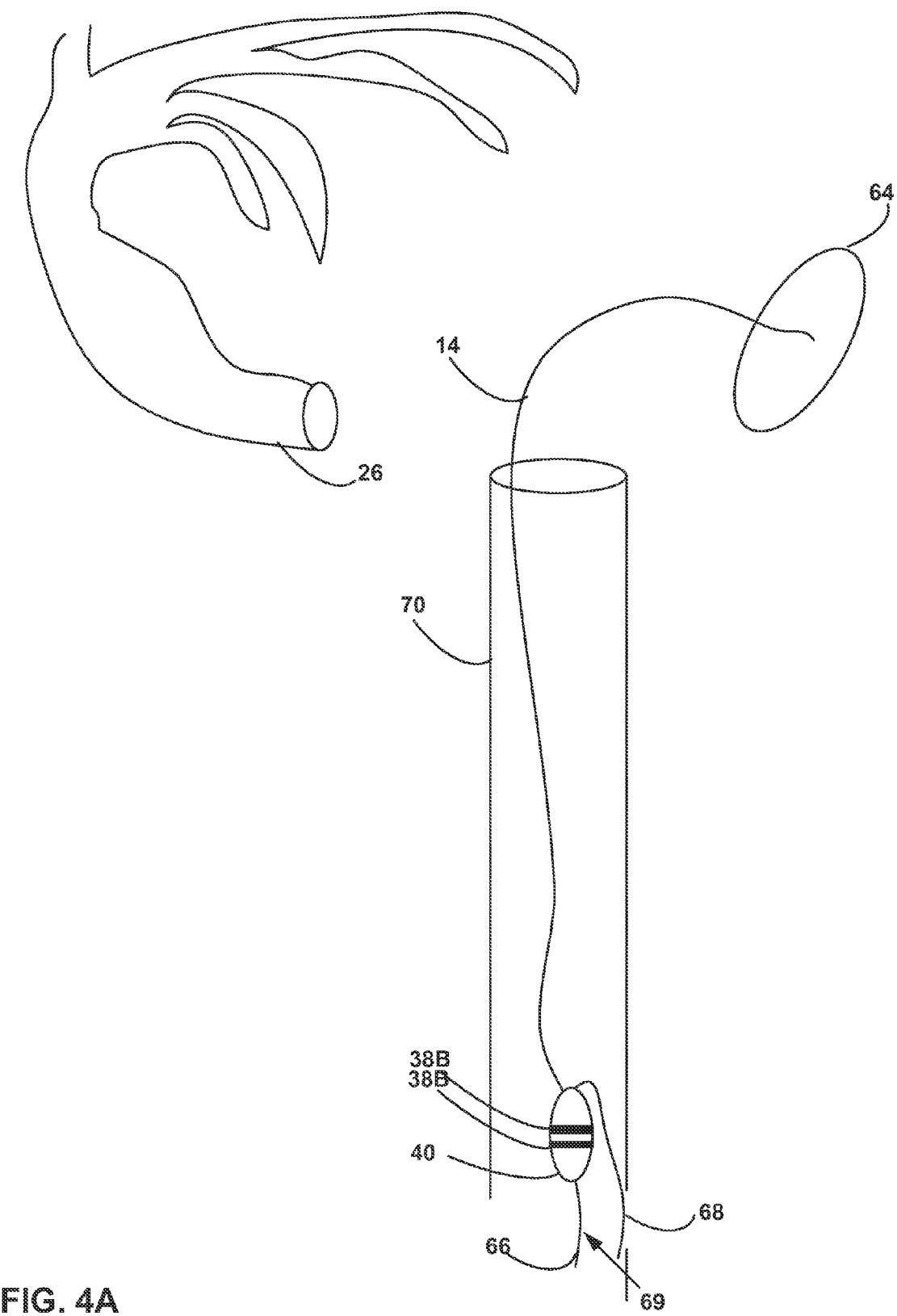
FIGS. 4A-4F illustrate various steps of an example method for implanting the system depicted in FIG. 1.
Figure 4B:
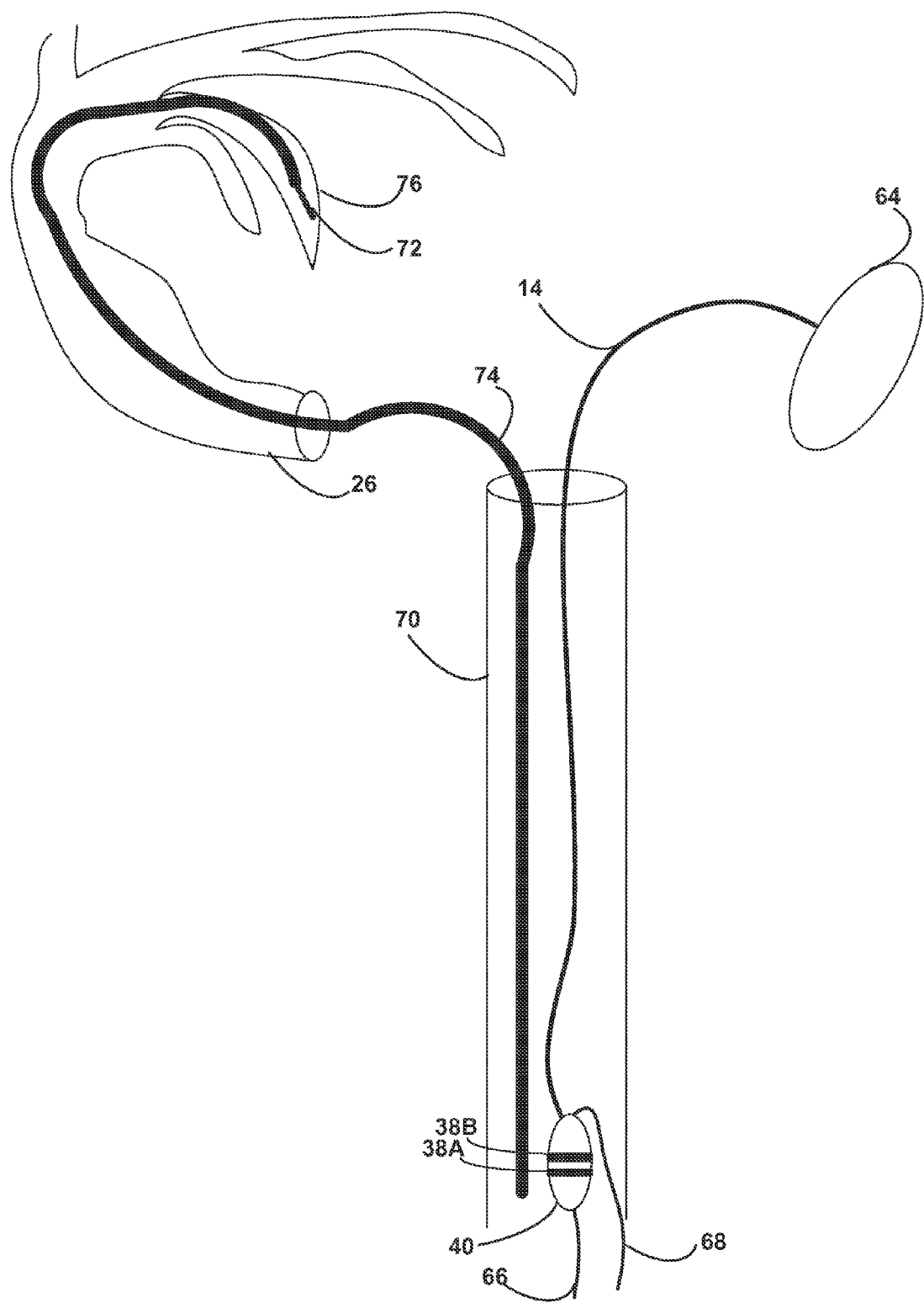

FIGS. 4A-4F illustrate a method of implanting system 10, and, in particular, housing 40 of extension 14 in a desired location within heart 18, e.g., to position one or both electrodes 38A, 38B to sense electrical activity of a particular chamber (e.g., the left ventricle) or deliver electrical stimulation to the particular chamber. In FIG. 4A, IMD 12 has been implanted in the right ventricle 16 (FIG. 1), and extension 14 enters right atrium 24 (FIG. 1) via tricuspid valve 64. A tether 69 comprising a first tether portion 66 and a second tether portion 68 is threaded through a hole in housing 40, the hole having a central axis that is substantially parallel (e.g., parallel or nearly parallel) to the longitudinal axis of extension 14. In some examples, first tether portion 66 is positioned on one side of housing 40 and extends from one end of the hole, and the second tether portion 68 is on the other side of housing 40 and extends form the other end of the hole.

In some examples, the first tether portion 66 is a different color than second tether portion 68 in order to help the clinician visually distinguish between the tether portions 66, 68. Tether 69 may be placed within the hole in housing 40 prior to implantation. For example, a manufacturer of extension 14 may install tether 69 in the hole of housing 40.

In some examples, housing 40 and tether 69 may be introduced into heart 18 via introducer 70. Introducer 70 may be introduced to heart 18 via the femoral vein (not shown). In the example shown in FIG. 4A, housing 40 and tether 69 are located within introducer 70. Introducer 70 is sized to receive extension 14 and tether 69, but is still relatively small in order to reduce the invasiveness of introducer 70. In some examples, introducer 70 may have a diameter of approximately 22 French, although other dimensions are contemplated. The diameter of introducer 70 may be the diameter of a cross-section of introducer 70 taken along an axis perpendicular to a longitudinal axis of introducer 70.

Guidewire 72 and catheter 74 may be used to define a pathway for extension 14 from introducer 70 to a location within coronary sinus 26 or another location within heart 18. In the example shown in FIG. 4B, guidewire 72 is introduced into a target vein 76 using a catheter 74, which may be guided to a location proximate coronary sinus 26 via introducer 70. In the example shown, target vein 76 branches from the coronary sinus 26. In some examples, the target vein is the coronary vein of the left ventricle.

Guidewire 72 and catheter 74 may have any suitable configuration. In some examples, guidewire 72 has a proximal guidewire portion and a distal guidewire portion having a different configuration than the proximal guidewire portion. The distal guidewire portion may be the portion of guidewire 72 that is furthest from the clinician when guidewire 72 is being inserted through tissue. In some examples, the distal guidewire portion (e.g., the distal most 20 cm) of guidewire 72 may be configured as a standard guidewire formed from any suitable wire (e.g., a nickel titanium wire). As an example, the distal guidewire portion may be formed from a wire that tapers in a distal direction from a diameter of about 0.014 inches to a diameter of about 0.012 inches, and becomes more flexible as it tapers. Other guidewire configurations and other guidewire dimensions may also be used, and may vary based on the implant location of housing 40 of extension 14.

In some examples, the proximal guidewire portion of guidewire 72 may be a suture thread, e.g., a 0.010 cm diameter suture thread, rather than a wire. To enable guidewire 72 to be pushed, rotated and pulled, the proximal guidewire portion may be is temporarily stiffened with a stiffening tube within which the proximal guide portion may be introduced. Catheter 74 may be configured to receive the stiffening tube. In some examples, the stiffening tube is formed from a biocompatible plastic material and has a 0.012 cm inner diameter, and a 0.030 outer diameter.

Figure 4C:
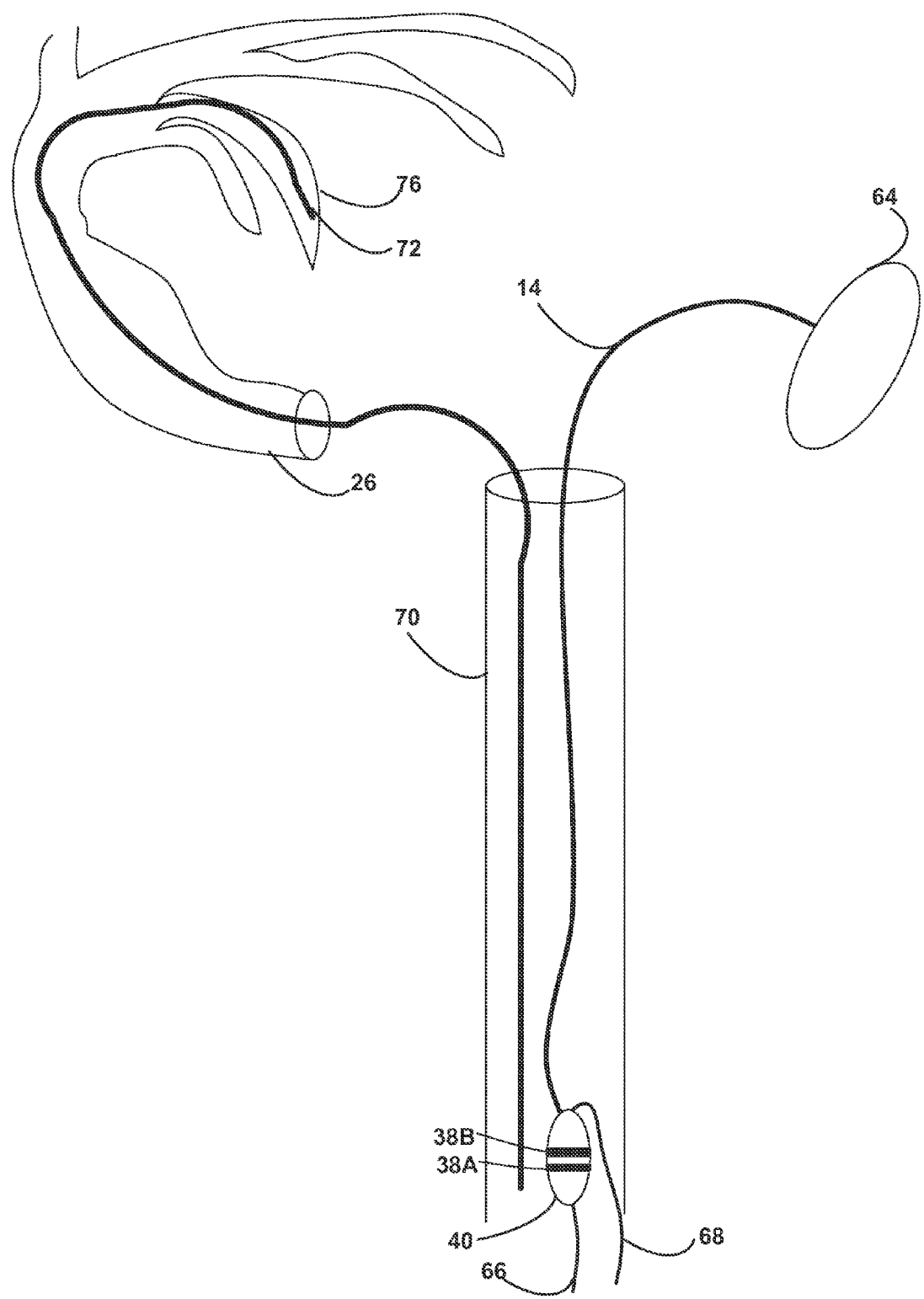

After the distal end of guidewire 72 is at target vein 76, as shown in FIG. 4C, both the stiffening tube (if used) and catheter 74 may be removed from patient 22, leaving guidewire 72 in place. In the step shown in FIG. 4D, first tether portion 66 is attached to the proximal end of the guidewire 72 (e.g., attached to the proximal guidewire's thread-like portion) at attachment point 80. For example, the proximal, threadlike, portion of guidewire 72 (portion 75 shown in FIG. 8, below) is intertwined with first tether portion 66 at point 80 to form one continuous thread. In some examples, a drop of instant adhesive may be applied in order to insure the integrity of the attachment.

Figure 4D:
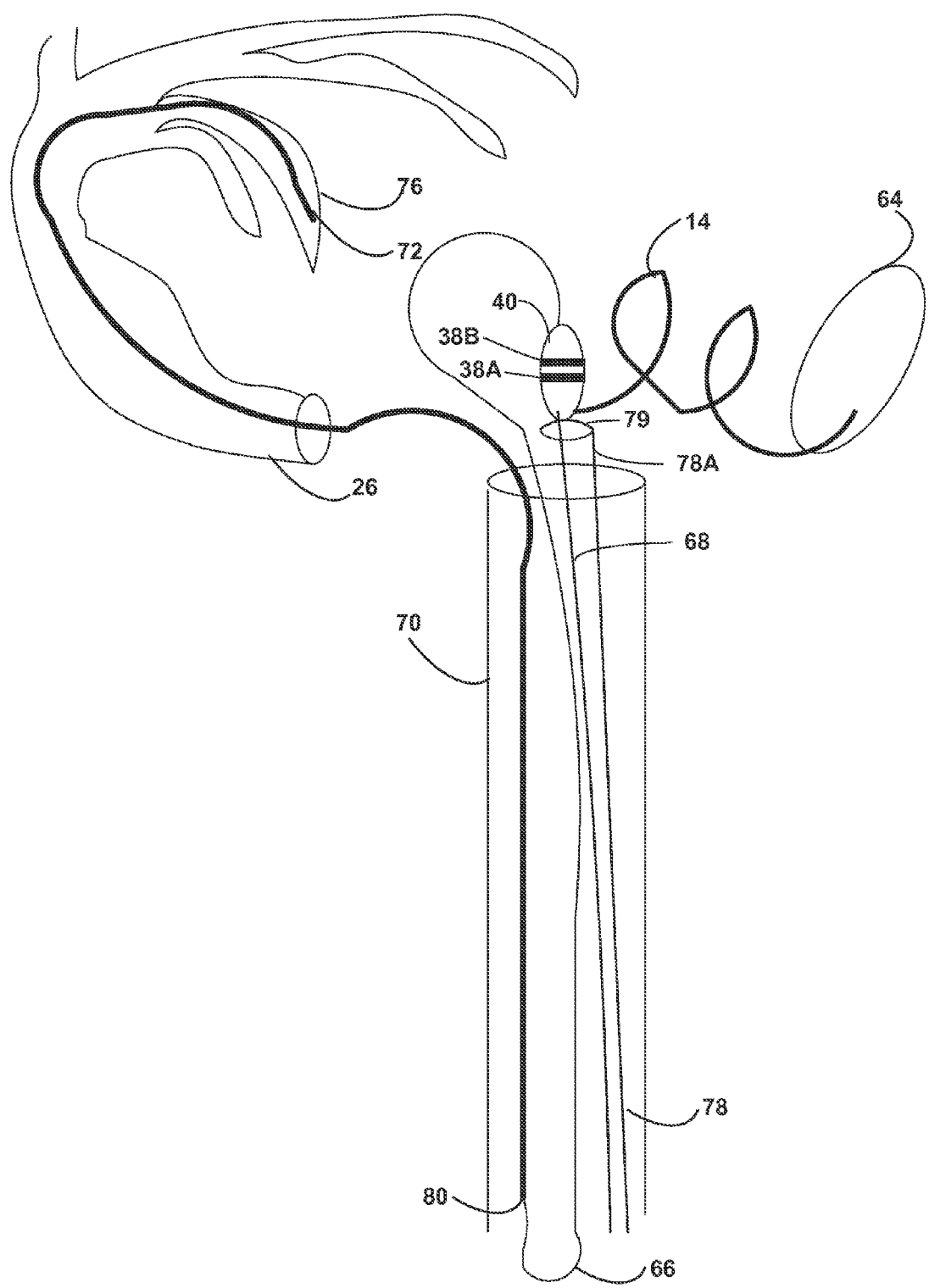

A clinician may introduce pusher 78 into introducer 70. In some examples, pusher 78 is made of wire. Pusher 78 may include eyelet 79 or another feature at a distal end 78A that is sized to receive tether 68, and engage with housing 40 to apply a force against housing 40 to move housing 40 in a direction away from introducer 70. In some examples, pusher 78 is made of stainless steel wire. In some examples, pusher 78 may be approximately 0.020 inches in diameter. In some examples, eyelet 79 is defined by one or more turns of the wire from which pusher 78 is formed. As shown in FIG. 4D, second tether portion 68 is threaded through eyelet 79 of pusher 78, thereby securing the relative lateral position between pusher 78 and tether 69. Pusher 78 may be moved along tether 69 (i.e., in a direction along a longitudinal axis of tether 69) to reach housing 40.

Figure 4E:
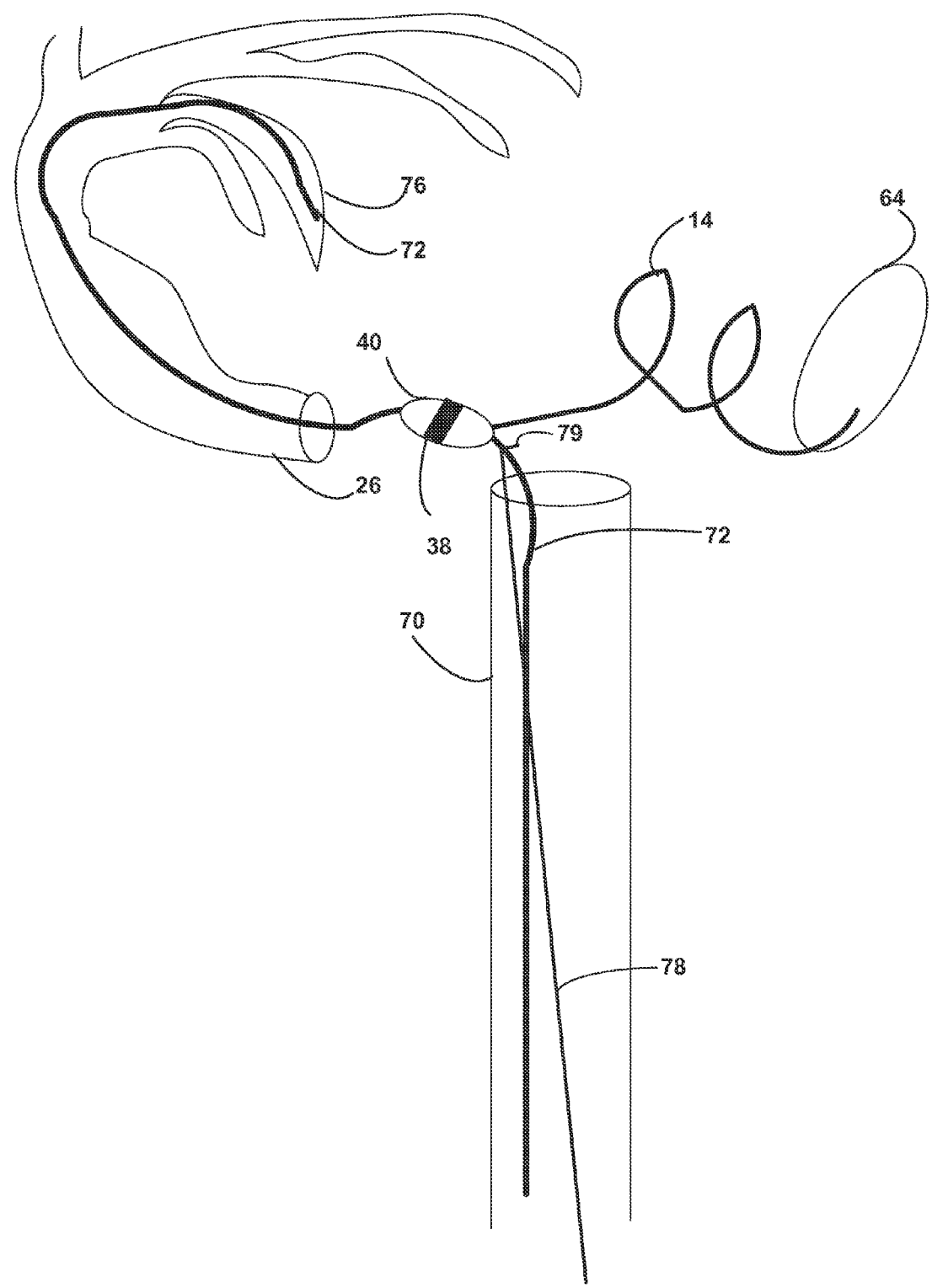

A clinician may pull on second tether portion 68, in a direction away from housing 40 (and, in some examples, in a direction away from patient 22). In some examples, the clinician may hold housing 40 in place with pusher 78 as second tether portion 68 is pulled. Prior to pulling on tether 69, tether 69 was extending through the hole defined by housing 40. As the clinician pulls on second tether portion 68, first tether portion 66 is pulled through the hole define by housing 40, such that the proximal guidewire portion of guidewire 72, which is attached to first tether portion 66, is fed through the hole defined by housing 69. In this way, guidewire 72 may replace tether 69, as shown in FIG. 4E. The proximal guidewire portion may be pulled through the hole defined by housing 69 because it is formed from a relatively flexible material, e.g., a suture thread, and not from the stiffer wire material with which first guidewire portion is formed from.

Guidewire 72 may be used to guide housing 40 to target vein 76. As described with respect to FIGS. 4A-4D, tether 69 provides a relatively quick and simple way to thread guidewire 72 through the hole in housing 40 while housing 40 is implanted in patient 22.

Figure 4F:
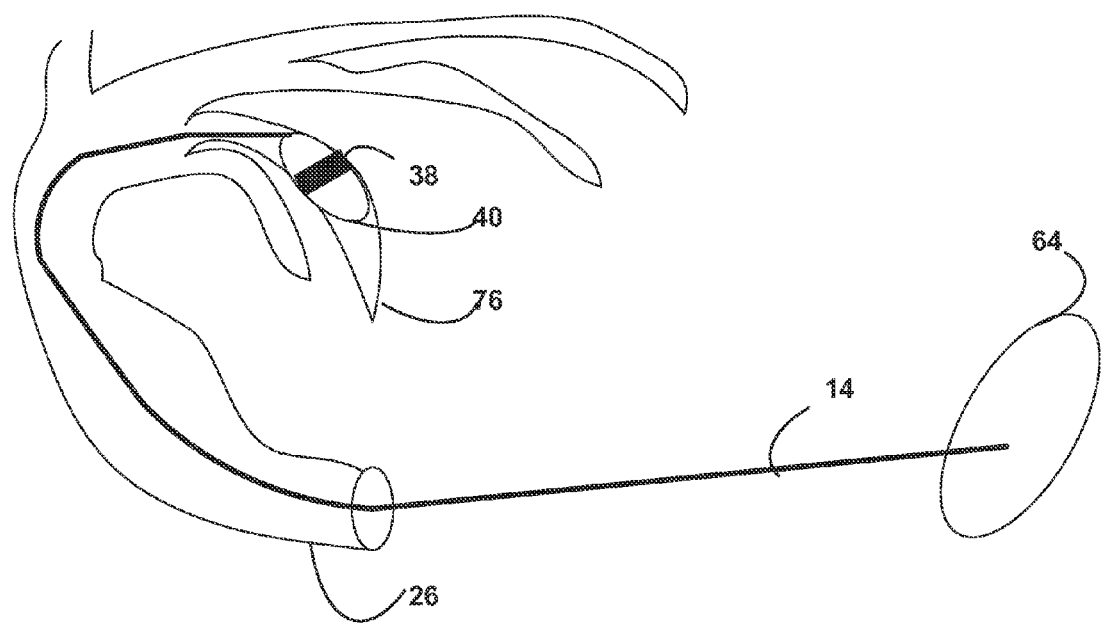

As further shown in FIG. 4E, pusher 78 is used to push housing 40 along guidewire 72 towards target vein 76 (or other desired location). In some examples, target vein 76 may be selected in order to provide biventricular pacing. As the electrodes 38A, 38B and housing 40 approaches the target vein 76, fine adjustment of the location of electrodes 38A, 38B relative to specific locations of heart 18 may be achieved by pushing on pusher 78 to move electrodes 38A, 38B distally (away from introducer 70), and by pulling on guidewire 72 and pusher 89 to move electrodes 38A, 38B in a proximal direction, towards introducer 70. After housing 40 is positioned proximate target vein 76 such that electrodes 38A, 38B are at a suitable location (e.g., as confirmed by any suitable testing of stimulation delivered via electrodes 38A, 38B or sensed by electrodes 38A, 38B) for delivering the pacing therapy to the left ventricle, pusher 78, guidewire 72, and introducer 70 are removed from patient 22. FIG. 4F depicts an example implantation setup of system 10.

Figure 5:
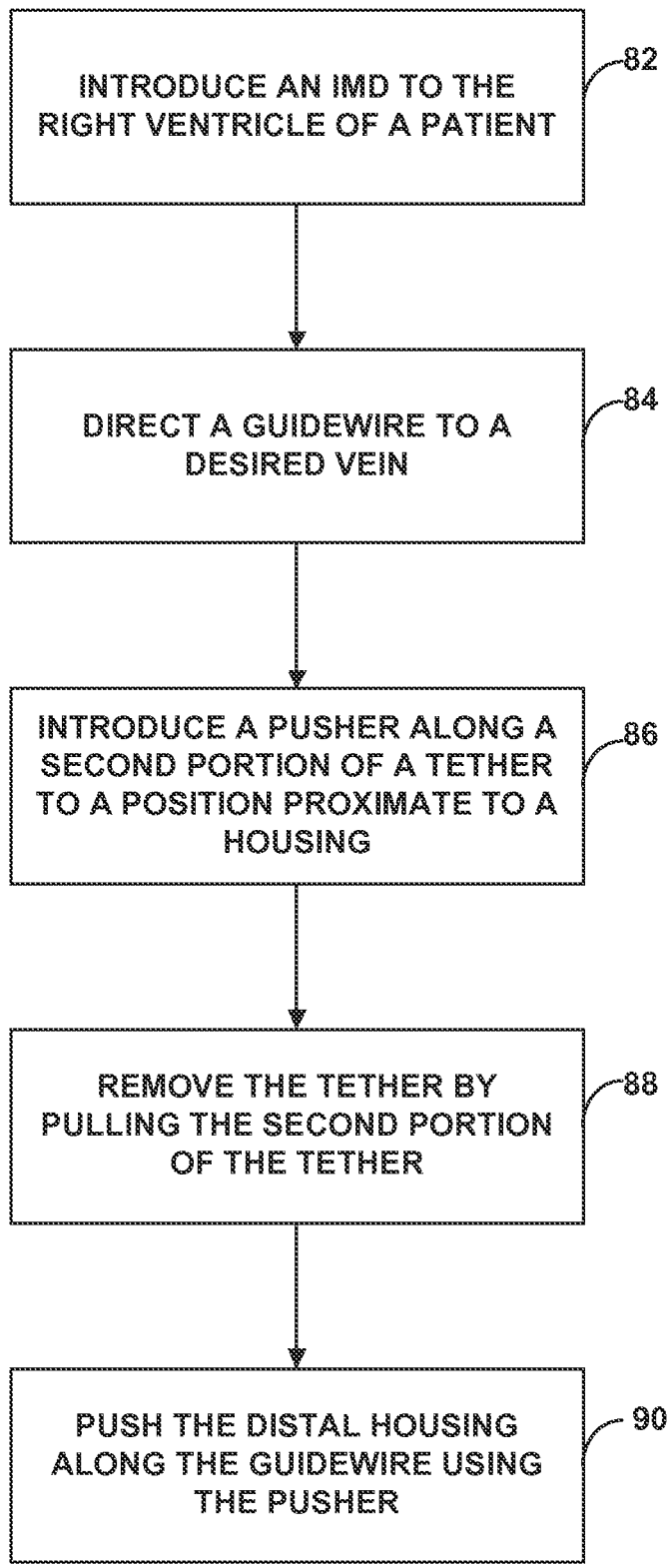
FIG. 5 is a flow chart illustrating an example method for implanting a cardiac pacing system in a heart of a patient.

FIG. 5 is a flowchart illustrating an example method for implanting cardiac pacing system 10 in a heart 18 of patient 22 to provide biventricular pacing. A clinician introduces an IMD 12 to the right ventricle 16 of patient 22 (82). In some examples IMD 12 may be introduced into the heart 18 via a femoral vein. In some examples, prior to implantation, pacing system 10 includes a tether, such as tether 69, which is threaded through a hole in housing 40 of extension 14. The clinician directs a guidewire 72 to a target vein (84). In some examples, the target vein may be off of the coronary sinus, and located so that when in place, electrodes 38A, 38B on housing 40 of extension 14 may provide pacing stimulation to the left ventricle. In some examples, a proximal end of the guidewire 72 may be attached to the first tether portion 66 of tether 69.

In some examples, the clinician introduces a pusher 78 along the second tether portion 68 of the tether to housing 40 (86). The clinician may the remove tether 69 from housing 40 by pulling the second tether portion 68 (88). Pulling on the second portion 68 of the tether results in guidewire 72 replacing tether 69 within the hole in housing 40. The clinician may then push housing 40 towards the target vein along the guidewire 72 using the pusher 78 (90). Pusher 78 and guidewire 72 are used to position electrodes 38A, 38B on housing 40 at a desired location, which may be selected in order provide adequate pacing stimulation to the left ventricle of heart 18.

Figure 6:
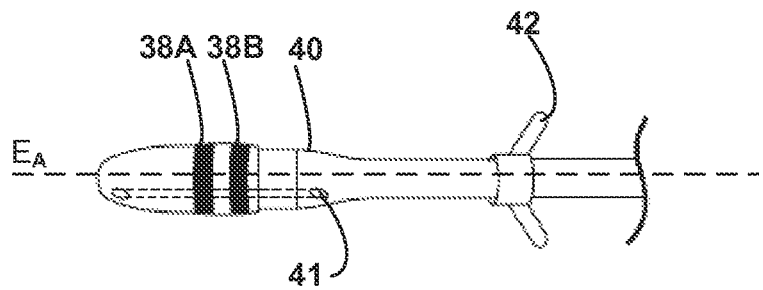
FIG. 6 is a conceptual illustration of a distal housing of an example extension.

FIG. 6 is a conceptual illustration of a distal housing 40. Distal housing 40 includes electrodes 38A and 38B and hole 41. Hole 41 is configured to accept tether 69 and/or guidewire 72. The longitudinal axis of hole 41 is parallel to the longitudinal axis $E_A$ of extension 14.

Figure 7:
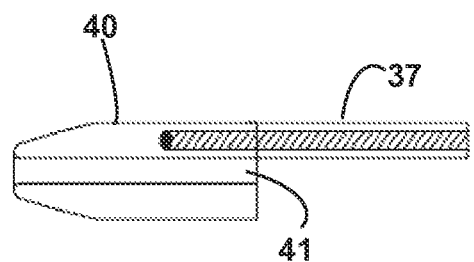
FIG. 7 is a conceptual illustration of a cutaway of an distal housing of an example extension.

FIG. 7 is a conceptual illustration of a cutaway of a distal housing 40 at the distal end of second extension portion 37. The cutaway of housing 40 shows hole 41. The longitudinal axis of hole 41 is parallel to the longitudinal axis of the second extension portion 37.

Figure 8:
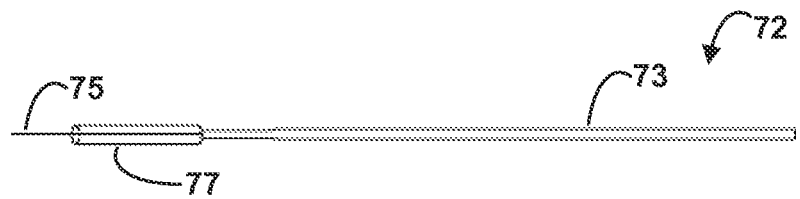
FIG. 8 is a conceptual illustration of an example guidewire and an example stiffener.

FIG. 8 is a conceptual illustration of guidewire 72 and stiffening tube 77. Guidewire 72 includes first guidewire portion 73 and a second guidewire portion 75. The first guidewire portion 73 resembles a standard guidewire and can be formed from a standard guidewire in some examples. In some examples, the first guidewire portion 73 is approximately 20 cm in length. The first guidewire portion may taper from 0.014 inches to 0.012 inches and becomes more flexible as it tapers. In some examples, the second guidewire portion 75 may be a thread. The thread may be approximately 0.010 inches in diameter. The second guidewire portion 75 may be encompassed by stiffening tube 77. Stiffening tube may be made of plastic. In some examples, stiffening tube 77 may have a 0.012 inch inside diameter, and a 0.030 inch outside diameter.

The techniques described in this disclosure, including those attributed to IMD 12, programmer 20, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

What is claimed is:

1. A method comprising:
introducing an implantable medical device to a first chamber of a heart of a patient via a femoral vein, wherein the implantable medical device is attached to an extension comprising a housing including at least one electrode, the housing defining a hole, and wherein a tether is threaded through the hole, the tether including a first tether portion and a second tether portion on an opposite side of the hole from the first tether portion;
directing a guidewire to a target vein, the guidewire comprising a first guidewire portion and a second guidewire portion, the second guidewire portion comprising a thread attached to the second tether portion;
introducing a pusher up the second tether portion to a position proximate to the housing;
removing the tether from the patient by at least pulling the second tether portion to replace the tether with the guidewire;
pushing the housing along the guidewire using the pusher.

2. The method of claim 1, wherein pushing the housing along the guidewire using the pusher comprises pushing the housing with the pusher to a location in a coronary sinus of the patient.

3. The method of claim 1, further comprising adjusting a location of the at least one electrode within the patient by at least one of:

pushing the pusher to move the housing in a distal direction, or pulling on both the guidewire and the pusher to move the housing in the proximal direction.

4. The method of claim 3, wherein the at least one electrode comprises a first electrode and the first chamber comprises a right ventricle, the implantable medical device comprising a second electrode, wherein adjusting the location of the at least one electrode comprises adjusting the location of the first electrode to be positioned in a left ventricle of the heart of the patient.

5. The method of claim 1, wherein the thread is encompassed by a stiffening tube, the method further comprising removing the stiffening tube from around the thread.

6. The method of claim 1, wherein introducing the implantable medical device into the first chamber of the heart of the patient comprises:

introducing a catheter into the chamber of the heart of the patient via the femoral artery; and introducing the implantable medical device into the chamber through the catheter.

\* \* \* \* \*